(12) United States Patent
Berlinger et al.

(10) Patent No.: US 10,201,717 B2
(45) Date of Patent: Feb. 12, 2019

(54) ONLINE PATIENT RECONSTRUCTION AND TRACKING FOR PATIENT SETUP IN RADIATION THERAPY USING AN ITERATIVE CLOSEST POINT ALGORITHM

(71) Applicant: Brainlab AG, Munich (DE)

(72) Inventors: Kajetan Berlinger, Munich (DE); Hagen Kaiser, Munich (DE)

(73) Assignee: Brainlab AG, Munich (DE)

( * ) Notice: Subject to any disclaimer, the term of this patent is extended or adjusted under 35 U.S.C. 154(b) by 217 days.

(21) Appl. No.: 15/328,470

(22) PCT Filed: Jul. 30, 2014

(86) PCT No.: PCT/EP2014/066373
§ 371 (c)(1),
(2) Date: Jan. 23, 2017

(87) PCT Pub. No.: WO2016/015760
PCT Pub. Date: Feb. 4, 2016

(65) Prior Publication Data
US 2017/0216626 A1    Aug. 3, 2017

(51) Int. Cl.
*A61N 5/10* (2006.01)
*G06T 7/33* (2017.01)
*G06T 7/521* (2017.01)

(52) U.S. Cl.
CPC .......... *A61N 5/1049* (2013.01); *A61N 5/1037* (2013.01); *G06T 7/33* (2017.01); *G06T 7/521* (2017.01); *A61N 2005/105* (2013.01); *G06T 2207/10012* (2013.01); *G06T 2207/10028* (2013.01); *G06T 2207/30088* (2013.01)

(58) Field of Classification Search
CPC .......... A61N 5/00; A61N 5/10; A61N 5/1049; A61N 5/1037; A61N 5/103; A61N 5/1048; A61N 2005/105; G06T 7/521; G06T 2207/10028; G06T 2207/30088; A61B 6/4258
USPC ................ 378/63, 65, 68, 95, 165, 205, 208
See application file for complete search history.

(56) References Cited

U.S. PATENT DOCUMENTS 7,348,974 B2    3/2008    Smith et al.
2011/0135190 A1    6/2011    Maad

FOREIGN PATENT DOCUMENTS

| GB | 2441550 | 3/2008 |
| GB | 2465297 | 7/2010 |
| WO | 2008029121 | 3/2008 |

OTHER PUBLICATIONS

European Patent Office, International Search Report and Written Opinion for PCT/EP2014/066373 dated Mar. 27, 2015.
Bauer, S. et al., Multi-Model Surface Registration for Markerless Initial Patient Setup in Radiation Therapy using Microsoft's Kinect Sensor, Pattern Recognition Lab, Department of Computer Science Jan. 1, 2000.

(Continued)

*Primary Examiner* — Jurie Yun
(74) *Attorney, Agent, or Firm* — Middleton Reutlinger

(57) ABSTRACT

A medical data processing method for tracking the position of a body surface of a patient's body, the method comprising determining, based on initial surface reflection data and reflection pattern registration data, body surface movement data describing whether the body surface has undergone a movement.

14 Claims, 4 Drawing Sheets

(56) References Cited

OTHER PUBLICATIONS

Biber, P. et al., The Normal Distributions Transform: A New Approach to Laser Scan Matching, WSI/GRIS, University of Tubingen Jan. 1, 2003.

Cayton, L. et al., Accelerating Nearest Neighbor Search on Manycore Systems, Max Planck Institute, Tubingen Germany and Microsoft Corp. Jan. 1, 2012.

Newcombe, R.A., KinectFusion: Real-Time Dense Surface Mapping and Tracking, IEEE International Symposium on Mixed and Augmented Reality, Science and Technology Proceedings Jan. 1, 2011.

Placht, S. et al., Fast Time-of-Flight Camera Based Surface Registration for Radiotherapy Patient Positioning, Am. Assoc. Phys. Med. 39 Jan. 1, 2012.

Segal, A.V. et al., Generalized-ICP Proceedings of Robotics: Science and Systems, Standford University Jun. 1, 2009.

Yang, J. et al., GO-ICP: Solving 3D Registration Efficiently and Globally Optimally, Beijing Lab of Intelligent Information Technology, Beijing Institute of Tecnology, Australian National University and NICTA Australia Jan. 1, 2013.

Bert, C. et al: Clinical experience with a 3d surface patient setup system for alignment of of partial-breast irradiation patents, Int. J. Radiation Oncology Biol. Phys. vol. 64, No. 4, pp. 1265-1274, Elsevier Inc. Jan. 1, 2006.

Brahme, A. et al.: 4d laser camera for accurate patient positioning, collision avoidance, image fusion and adaptive approaches during diagnostic and therapeutic procedures, Medical Physics 35, 1670, American Association of Physicists in Medicine Apr. 8, 2008.

Gelfand, N. et al.: Geometrically stable sampling for the ICP algorithm, Proceedings of the Fourth International Conference on 3-D Digital Imaging and Modeling Oct. 1, 2003.

Humenberger, M., Zinner, C., Weber, M., Kubinger, W., Vincze, M: A fast stereo matching algorithm suitable for embedded real-time systems, Elsevier, Computer Vision and Image Understanding 114, pp. 1180-1202 Nov. 1, 2010.

Lindl, B. L. et al.: A new topometric patient positioning and tracking system for radiation therapy based on structure white light, Medical Physics 40, 042701, American Association of Physicists in Medicine Jan. 1, 2013.

Peng, J. L. et al.: Characterization of a real-time surface image-guided stereotactic positioning system, Medical Physics 37, 5421, American Association of Physicists in Medicine Jan. 1, 2013.

Stieler, F. et al.: A novel surface imaging system for patient positioning and surveillance during radiotherapy, Department of Radiation Oncology, Strahlentherapie and Onkologie 11 Jan. 1, 2013.

Welford, B. P.: Note on a method for calculating corrected sums of squares and products, American Statistical Association and American Society for Quality, Technometrics, vol. 4, No. 3, pp. 419-420 Jan. 1, 1962.

Torsten Moser et al., Technical performance of a commercial laser surface scanning system for patient setup correction in radiotherapy, Physica Medica, Acta Medica Edizioni E Congressi, Rome, IT, vol. 27, No. 4, pp. 224-232 Oct. 3, 2010.

ONLINE PATIENT RECONSTRUCTION AND TRACKING FOR PATIENT SETUP IN RADIATION THERAPY USING AN ITERATIVE CLOSEST POINT ALGORITHM

The present invention is directed to a medical data processing method for tracking the position of a body surface of a patient's body in accordance with claim 1, a corresponding computer program, a computer running that program and a radiotherapy system or radiosurgery system comprising that computer.

When conducting a medical procedure such as radiotherapy or radiosurgery on a patient, it is desirable to have precise knowledge of the position of specific anatomical body parts of the patient's body at particular at times when the patient is to be irradiated with treatment radiation. A problem may arise if the patient spontaneously moves after he has been properly placed on the treatment table. In that case, it is desirable to quickly gather precise information about the new position of the patient's body for example relative to the treatment beam so as to ensure that despite the spontaneous movement, the target is properly irradiated with treatment radiation.

For example to solve the problem of spontaneous patient movement, VisionRT has devised their product AlignRT®, and C-RAD has devised their product Catalyst, which use a range cameras for tracking the patient's body in order to build a three-dimensional reconstruction of the patient's body. This reconstruction is registered either against a preoperatively acquired computer tomography or against itself in order to track the patient's position and thereby determine whether any movement has occurred. These approaches are used to position the patient relative to a machine isocentre of a linear accelerator used as a treatment device. If no computer tomography surface is used, the patient is tracked only relative to the first frame acquired by the range cameras. It is currently state of the art to use the iterative closest point (ICP) algorithm.

The following publications also contain teachings regarding the state of the art:
WO 2008/029121 A1
GB 2465297 B
U.S. Pat. No. 7,348,974 B2
US 2011/35190 A
Bauer, S. et al., Multi-Model Surface Registration for Markerless Initial Patient Setup in Radiation Therapy using Microsoft's Kinect Sensor, 15$^{th}$ International Conference on Medical Image Computing and Computer Assisted Intervention (MICCAI 2012)
Biber, P. et al., The Normal Distributions Transform: A New Approach to Laser Scan Matching IROS 2003, 2003 IEEE/RSJ International Conference on Intelligent Robots and Systems (vol. 3), pp. 2743-2748, ISBN 0-7803-7860-1
Cayton, L. et al., Accelerating Newest Neighbor Search on Manicore Systems, IPDPS'12, Proceedings of the 2012 IEEE 26$^{th}$ International Parallel and Distributed Processing Symposium, pp. 402-413, ISBN 978-9-7695-4675-9
Newcombe, R. A., KinectFusion: Real-Time Dense Surface Mapping and Tracking, IEEE International Symposium on Mixed and Augmented Reality 2011, Science and Technology Proceedings 26-29 October, Basel, Switzerland, ISBN 978-1-4577-2184-5
Placht, S. et al., Fast Time-of-Flight Camera Based Surface Registration for Radiotherapy Patient Positioning, Med. Phys. 39(1) January 2012, pp. 4-17
Segal, A. V. et al., Generalized-ICP Proceedings of Robotics: Science and Systems, June 2009
Yang, J. et al., GO-ICP: Solving 3D Registration Efficiently and Globally Optimally, 2013 IEEE International Conference on Computer Visions (ICCV), pp. 1457-1464, DOI: 10.1109/ICCV.2013.184

Further state of the art is represented by:
Bert, C. et al.: Clinical experience with a 3d surface patient setup system for alignment of partial-breast irradiation patients, International Journal of Radiation Oncology*Biology*Physics 64(4) (2006) 1265-12743
Brahme, A. et al.: 4d laser camera for accurate patient positioning, collision avoidance, image fusion and adaptive approaches during diagnostic and therapeutic procedures. Med. Phys. 35(5) (2008) 1670-1681
Gelfand, N. et al.: Geometrically stable sampling for the ICP algorithm, in: Fourth International Conference on 3D Digital Imaging and Modeling (3DIM), October 2003
Humenberger, M., Zinner, C., Weber, M., Kubinger, W., Vincze, M.: A fast stereo matching algorithm suitable for embedded real-time systems, Comput. Vis. Image Underst. 114(11) (November 2010) 1180-1202
Lindl, B. L. et al.: A new topometric patient positioning and tracking system for radiation therapy based on structured white light. Med. Phys. 40(4) (2013) 042701
Peng, J. L. et al.: Characterization of a real-time surface image-guided stereotactic positioning System, Med. Phys. 37(10) (2010) 5421-5433
Schaller, C., Adelt, A., Penne, J., Hornegger, J.: Time-of-flight sensor for patient positioning, Proceedings of SPIE, vol. 7258, 2009
Stieler, F. et al.: A novel surface imaging system for patient positioning and surveillance during radiotherapy: A phantom study and clinical evaluation, Strahlenther. Onkol. (2013) 189: 938-944
Welford, B. P.: Note on a method for calculating corrected sums of squares and Products, Technometrics 4(3) (1962) 419-420

Currently available systems and methods try to track the position of the patient as fast and as accurately as possible using structured light surface reconstruction. Highly accurate structure light systems are not able to achieve real time performance, though. Real time surface reconstruction systems are not very accurate.

Real time tracking is a concern in radiation therapy since one wants to react to spontaneous movement of the patient as fast as possible. Current systems prefer the high-speed approach over accuracy. To nevertheless achieve high accuracy, the patient's complete body surface is usually tracked and at least three customized high performance cameras are used. Furthermore, the systems track the patient relative to one frame gathered by the high performance cameras if not used with a computer tomography image surface as an initial comparison. The tracking procedure is therefore dependent on a reference surface that is based on only one measurement. Non-coplanar treatment fields can cause the patient to be moved as significant rotational amount which causes big parts of the patient to become occluded if the patient is observed from only one perspective. In this context, it is noted that the ICP algorithm is prone to fall into local minima when a reference surface is registered against a surface which has a big translational or rotational offset. The same is true if the reference surface is only partially congruent with the target surface. Therefore, currently available products such as AlignRT® and Catalyst try to capture as much of the patient's body surface as possible. This is achieved by using at least three range cameras that deliver patient reconstructions from three different angles. Using this technique, for example the Catalyst system is able to achieve full patient coverage independent of the rotational position of the treatment bed. The three reconstructions are joined (for example, fused) to one patient model. The AlignRT® systems use a special stitching technique to exclude any overlap between the reference surface and the target surface and stich the reconstructions together at defined separating lines. The aforementioned publication by Placht et al. proposes patient positioning using a single camera. To achieve consistent patient tracking over big rotational movements, the camera uses a key point-based pre-alignment of the surface before applying the ICP algorithm for refinement. This is computationally expensive and prone to noise.

The present invention provides a method for tracking the position of a patient's body surface which in one embodiment allows for efficient, continuous and fast updates of the positional information about the position of the body surface also in case part of the body surface is outside the field of view of the camera after spontaneous movement of the patient's body has occurred.

Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can for example be added to said other embodiment.

The present invention has for example application in a radiotherapy system, such as with the ExacTrac® radiotherapy system supplied by Brainlab AG. In this context, the integration of the surface-based positioning technology would allow a markerless setup workflow application with ExacTrac®. For example, the present invention in one embodiment would allow for the integration of range cameras directly into the flat-panels of the radiotherapy system so as to achieve a stable surface registration with a limited field of view and big shifts, which is a requirement for non-coplanar positioning. In doing so, the conventional body marker-based positioning use so far with ExacTrac® could be replaced by an automatic surface-based prepositioning.

EXEMPLARY SHORT DESCRIPTION OF THE PRESENT INVENTION

In the following, a short description of the specific features of the present invention is given which shall not be understood to limit the invention only to the features or a combination of the features described in this section.

The present invention relates in one example to a method for determining whether a patient's body has been placed ready for radiotherapy or radiosurgery. The method encompasses detection of light reflections from the surface of the body by scanning the body with a laser device and receiving the laser signals reflected from the body which serve to grow a reconstruction of the surface which allows to detect whether subsequently received positions of reflection points on the surface have a predetermined spatial relationship to previously received positions of the reflection surface. For achieving this aim and to grow a reconstruction of the entire surface visible to the light emitting unit and the reflection detection unit used for implementation of the method, the positional information received in subsequent scans of the surface (later "generations") is given lower weights than the previously received information (earlier "generations"). If it is for example determined that a set of positions determined for a later generation does not sufficiently fit into a set of positions gathered for an earlier (for example, the immediately preceding generation), a movement of the body surface can be deduced. This may for example be the case if the positions of reflection points of the later generation have a variance compared to the positions of reflection points of the earlier generation which is larger than a maximum allowed (for example desired) variance.

GENERAL DESCRIPTION OF THE PRESENT INVENTION

In this section, a description of the general, in some cases particular preferred, features of the present invention is given.

In a first aspect, the disclosed method is a data processing method, such as for example a medical data processing method, which is suitable for tracking the position of the body surface of a patient's body. The method for example comprises the following steps which are for example constituted to be executed by a computer (further particularly, all of the steps of the method in accordance with the invention are constituted to be executed by a computer).

For example, initial surface reflection data is acquired which describes (for example defines) a first reflection pattern of reflection points. The first reflection pattern for example is an initial reflection pattern, for example it is the first reflection pattern acquired within execution of the method. The reflection points constitute for example optical signals which are reflected from an initial part of the body surface. For example, the body surface is irradiated with a light in the optical spectrum (for example, in the infrared, or visible wavelength ranges), for example by scanning (i.e. irradiating for example at consecutive positions) the body surface with a light emitting unit such as e.g. a laser device at a rather high scanning frequency, e.g. at least 5 Hz, for example a frequency lying in the interval from 5 Hz to 20 Hz including the boundary values (for example, 5 Hz). The light reflections from the body surface are detected by a reflection detection unit such as a camera, for example by a stereoscopic camera. The reflection detection unit for example is sensitive in the infrared wavelength spectrum, it is able to detect light signals having a wavelength in the infrared wavelength spectrum. The stereoscopic camera for example has a known distance between the camera lenses, which known distance together with the azimuth of the reflections relative to the stereoscopic camera (for example relative to a centre plane of the stereoscopic camera which is located for example half way in between the two lenses) allows to determine the distance of the points on the body surface (the so-called reflection points) from which the optical signals are reflected by way of for example triangulation. Thereby, the positions of the reflection points of the initial part can be determined and are acquired by the disclosed method. For example, the positional information processed by the method is defined in three dimensions; as a further example, the first reflection pattern and the second reflection pattern are represented by three-dimensional point clouds.

Alternatively, the reflection detection unit may be a time-of-flight camera or a laser scanner which receives depth information for the position of the reflection point from the time the light requires from emission over reflection to detection or deformation of the laser reflection trajectory, respectively.

The initial part is given this name because the optical signals reflected from it are designed to serve as a first reference (the "initial first reflection pattern") to which the following scanning measurements will be compared in order to determine whether there has occurred any change in the positions of the reflection points and therefore any movement of the body surface. Furthermore, the subsequent scan frames will be adhered ("stitched" or "joined") to the initial first reflection pattern if they comprise information defining a part of the body surface which is not identical but for example adjacent to the initial part. In other words, the initial parts serve as a dataset to which further datasets derived from later scan measurements are stitched in order to "grow" a reconstruction of the body surface. The reconstruction is made up of for example a dataset defining a set of coordinates which define the positions of the reflection points. In other word, the reflection points are embodied by the points of a dataset defining a "point cloud" defining the positions of each point from which a reflection has been detected during the scanning. The number of points (the number of members of the dataset) in the point cloud is set to be balanced the detection frequency of the stereoscopic camera so as to avoid unnecessary computational effort or complications due to too large a data load. The detection frequency of the stereoscopic camera is as chosen to lie at for example at least 2 Hz. The number of points is for example chosen to lie in the interval of about 20,000 to about 40,000.

For example, subsequent surface reflection data is acquired which describes (for example defines) a second reflection pattern of reflection points of optical signals reflected from a subsequent part of the body surface and the positions of the reflection points of the subsequent part at which the optical signals are reflected. The subsequent surface reflection data is generated for example after the generation of the initial surface reflection data (i.e. when the initial surface reflection data has been generated). The subsequent part is identical or is not identical to the initial part. If it is not identical to the initial part, it is for example neighbouring, i.e. adjacent, or joining, and disjunct from, or partly overlapping with the initial part.

For example, body surface reconstruction data is determined which describes (for example defines) a positional reconstruction of the body surface. The body surface reconstruction data is determined for example by determining, based on (for example from) the initial surface reflection data and the subsequent surface reflection data, reflection pattern registration data. The reflection pattern registration data describes (for example defines) a positional registration of the second reflection pattern with the first reflection pattern. Such a positional registration is for example a mapping, for example a coordinate mapping. Alternatively or additionally, a registration is understood to be a transformation of two datasets (comprising for example positional information) into a common coordinate system. The reflection pattern registration data is determined for example based on (for example by) searching the second reflection pattern for at least one nearest neighbouring reflection point in the second reflection pattern for the reflection points (i.e. for each reflection point) in the first reflection pattern. This search is for example performed by determining, for (for example at) each reflection point in the second reflection pattern, whether it (i.e. the reflection point) is the nearest neighbour to a currently considered reflection point in the first reflection pattern. The reflection point which in a single (specific) iteration of this search is being analysed is hereinforth also called current reflection point of the second reflection pattern. Furthermore, the search includes the following two (mutually exclusive) alternative steps:

- Either, the current reflection point of the first reflection pattern is updated by the current reflection point of the second reflection pattern if it is determined that the current reflection point of the second reflection pattern is the nearest neighbour to a reflection point in the first reflection pattern. Updating the current reflection point of the first reflection pattern encompasses for example changing and/or replacing the position of the current reflection point of the first reflection pattern by an average (for example, a weighted average) position between the position of the current reflection point of the first reflection pattern and the position of the current reflection point of the second reflection pattern. The concept of weighting is explained further below.
- Or, if it is determined that the current reflection point of the second reflection pattern is not a nearest neighbour to a reflection point in the first reflection pattern, it is determined whether the current reflection point of the second reflection pattern is within a predetermined distance from a reflection point of the first reflection pattern, determining. This alternative also includes the following two (mutually exclusive) sub-alternatives:
  - Either, if it is determined that the current reflection point of the second reflection pattern is within a predetermined distance from a reflection point of the first reflection pattern, the current reflection point of the second reflection pattern is added to the reconstruction (i.e. to the dataset defining the point cloud, the current reflection point of the second reflection pattern is added to the point cloud).
  - Or, if it is determined that the current reflection point of the second reflection pattern is not within a predetermined distance from a reflection point of the first reflection pattern, the current reflection point of the second reflection pattern is discarded (i.e. not immediately used as an input for further data processing). The step of discarding the current reflection point of the second reflection pattern—according to one specific embodiment—comprises storing the current reflection point of the second reflection pattern for future use as initial surface reflection data (i.e. for adding it to the point cloud in a later iteration of the method).

For example, body surface movement data is then determined, based on the initial surface reflection data and the reflection pattern registration data. The body surface movement data describes (for example defines) whether the body surface has undergone a movement (or not). For example, the body surface movement comprises information indicating whether the body surface has changed its position (for example relative to the reflection detection unit).

For example, the above-describes step of determining whether the current reflection point of the second reflection pattern is within a predetermined distance from a reflection point of the first reflection pattern comprises determining a spatial neighbourhood around a centre point between the current reflection point of the second reflection point and the current reflection point of the first reflection pattern. As a further example, that step also comprises determining a characteristic size of the neighbourhood, for example its diameter.

For example, updating the current reflection point of the first reflection pattern includes assigning a weight to the current reflection point of the first reflection pattern. As a further example, the (positions of the) reflection points of the first reflection pattern are assigned weights and (the position of) any current reflection point of the second reflection pattern which is to be stored is assigned a lower weight than the (positions of) the reflection points already contained in the first reflection pattern. For example, a current reflection point of the second reflection pattern having a statistically larger distance from the current reflection point of the first reflection pattern is assigned a lower weight than a current reflection point of the second reflection pattern having a statistically smaller distance from the current reflection point of the first reflection pattern. This means that reflection point gathered during later scanning iterations and having a higher statistical spatial variance are weighted lower to increase the reliability of the disclosed method. Furthermore, a current reflection point of the second reflection pattern having a statistically larger distance from the current reflection point of the first reflection pattern is not included in the reconstruction and is not stored for future use as initial surface reflection data.

In a second aspect, the disclosed method is directed to a method of controlling a radiotherapy system or radiosurgery system. In a first embodiment of the method of controlling a radiotherapy system or radiosurgery system, the method of controlling a radiotherapy system or radiosurgery system comprises the following preferred steps:

the steps of the method described in the above text; and
at least one of the following steps:
  Determining, based on the body surface movement data, treatment beam data describing whether to activate or deactivate a treatment beam. For example if analysis of the information contained body surface movement data results in a determination that the body surface has moved at least to a predetermined degree in at least one of space and time, activation of the treatment beam may be impeded, or an already activated treatment beam may be switched off. This may be advantageous to detect the point in time after placing the patient on the table of a radiotherapy or radiosurgery system at which the patient has calmed down and stopped moving.
  Determining, based on the body surface movement data, patient support unit control data for controlling a patient support unit of the radiotherapy system or radiosurgery system, respectively, to move such that the movement of the body surface is compensated for in view of for example positional information contained in predetermined treatment plan data describing a treatment plan for radiotherapy or radiosurgery, respectively. For example, if analysis of the information contained body surface movement data results in a determination that the body surface has moved at least to a predetermined degree in at least one of space and time, the patient (for example the table on which he is placed) may be moved so that the patient reaches a position defined by the treatment plan data. This constitutes a repositioning procedure for bringing the patient back into a desired position which he may have left due to spontaneous movement.

The second aspect of the disclosed method is also directed to a second embodiment of the method of controlling a radiotherapy system or radiosurgery system, comprising:

the method according to any one of the preceding claims (for example, this second embodiment may comprise but does not necessarily require the first embodiment of the method of controlling a radiotherapy system or radiosurgery system); and determining, based on the body surface movement data, verification imaging control data for activating an imaging unit of the radiotherapy system or radiosurgery system, respectively, to generate medical image data for verification of the position of a treatment target. For example, two-dimensional x-ray images may be generated by activating a two-dimensional x-ray device (e.g. a fluoroscope) operably coupled to the radiotherapy or radiosurgery system. These images may be used to visually (by user interaction) or automatically (by executing an automatic image analysis data processing method) judge whether the patient is lying correctly if spontaneous movement has been detected and/or after the patient has been re-positioned.

In a third aspect, the invention is also directed to a program which, when running on a computer, causes the computer to perform one or more or all of the method steps described herein and/or to a program storage medium on which the program is stored (for example in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

In a fourth aspect, the invention is directed to a radiotherapy system or radiosurgery system, comprising:
  a treatment beam source (comprising e.g. a linear accelerator, an x-ray tube or a radioactive agent for emission of treatment radiation);
  a patient support unit (such as a table, for example a treatment table, or a so-called couch, the position of which is for example automatically controllable);
  a light emitting unit to emit light for generating the optical signals to be reflected;
  a reflection detection unit, for example a stereoscopic camera, for detecting the reflected optical signals; and
  the aforementioned computer according to the preceding claim, the computer being operatively connected to the reflection detection unit and for example also the light emitting unit, the treatment beam source and the patient support unit to execute the aforementioned program which comprises code means for executing the method according to at least one of the first and second aspects of the disclosed method.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

The present invention in one example does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or for example comprise or encompass any surgical or therapeutic activity. The invention is instead directed for example to a method of detecting the position of a body surface without the need for any surgical or therapeutic activity for executing the method. No surgical or therapeutic step is necessitated or implied by carrying out the invention.

DEFINITIONS

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is for example a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The present invention relates to for example the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, for example radiation beams, to treat parts of a patient's body, which are therefore also referred to as treatment beams. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, for example in the field of oncology. For treating cancer for example, parts of the body comprising a pathological structure or tissue such as a tumour are treated using ionising radiation. The tumour is then an example of a treatment body part.

The method in accordance with the invention is for example a data processing method. The data processing method is for example performed using technical means, for example a computer. The data processing method is for example constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is for example connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is for example operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. For example, the acquiring step does not involve an invasive step which would represent a substantial physical interference with the body, requiring professional medical expertise to be carried out and entailing a substantial health risk even when carried out with the required professional care and expertise. For example, the step of acquiring data, for example determining data, does not involve a surgical step and for example does not involve a step of treating a human or animal body using surgery or therapy. In order to distinguish the different data used by the present method, the data are denoted (i.e. referred to) as "XY data" and the like and are defined in terms of the information which they describe, which is then for example referred to as "XY information" and the like.

DESCRIPTION OF THE FIGURES

In the following, the invention is described with reference to the enclosed figures which represent preferred embodiments of the invention. The scope of the invention is not however limited to the specific features disclosed in the figures, wherein.

Figure 1:
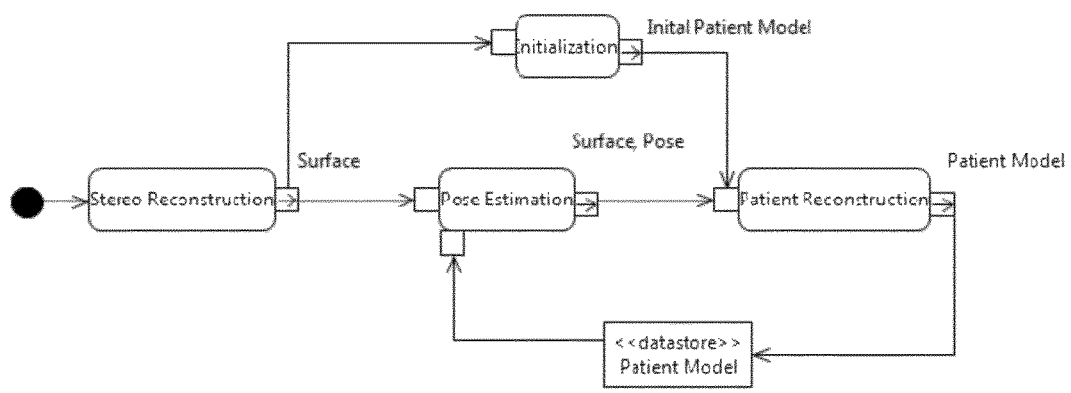
FIG. 1 is a box diagram showing the functional blocks of the method in accordance with the first aspect of the disclosed method.

From FIG. 1 it is clear that, our patient positioning pipeline is separated into three threads: (a) stereo reconstruction, (b) tracking, and (c) "on the fly" patient model reconstruction. These three tasks can be performed independently as they have different demands regarding performance respectively. The tracking task is developed in real-time. The inventive method optimizes a global patient model where the information collected by the surface acquisition is accumulated to receive a more reliable reference surface constantly over time ("on the fly" reconstruction), which is used to be registered to the current measurement.

Figure 2:
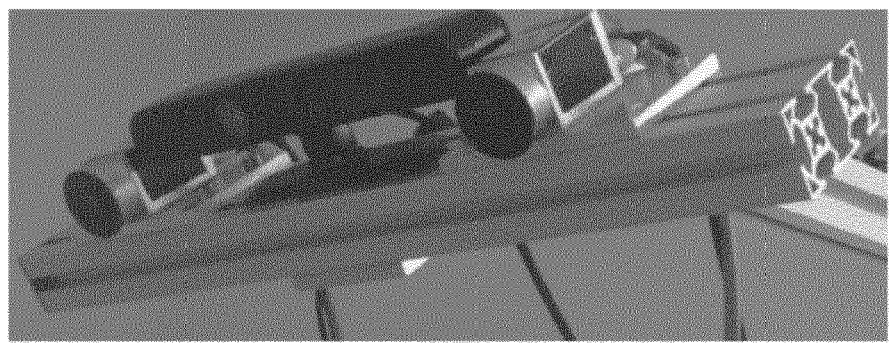
FIG. 2 shows a rig (embodied by a stereo rig) holding the light emitting unit (embodied by a speckle projection system) and the reflection detecting unit.
Figure 3:
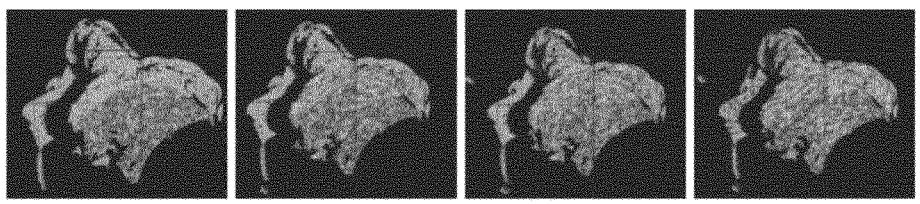
FIG. 3 shows the principle of growing the reconstruction of the body surface by surface evolution.

Surface Acquisition: As a range imaging device which the disclosed method uses a reflection detection unit stereo-rig made of two Basler cameras a, b with a resolution of 1604×1204 pixels. Each camera lens is augmented with an IR filter. The cameras are mounted with baseline (i.e. distance between the lenses) of 12 cm. To this setup, an IR laser is added which has a fixed diffraction grating as available in the Kinect sensor. It projects a speckle pattern on the patient surface. The pattern is invisible to the patient and thus will not cause irritation unlike the pattern used by the system described Peng et al. In accordance with the invention, the stereo-rig is mounted to the ceiling near the LINAC gantry (i.e. the treatment beam source) at 1 m distance to the machine isocentre. This is an optimal position regarding compatibility with other scanning systems that are usually also mounted in the treatment room and need a line of sight to the machine isocentre. By changing the exposure of the camera, the weight of the points detected in the projected pattern can be easily changed compared to points detected in naturally textured regions (see FIG. 2). At time k the stereo rig consisting of camera a and b acquires simultaneously two images from the projected pattern. To calculate the range image $RI_k$ which is a set of point measurements $p_{u;v} \in R^3$ indexed by the originating pixel (u; v) from camera a, the disclosed method uses the implementation of the census transform algorithm explained by Humenberger et al. The algorithm has a low memory footprint and is fast while still yielding satisfying accuracy and thus is suited to be implemented on embedded platforms, which would reduce the size of the device even more. To match a pixel (u; v) from camera a to camera b the algorithm searches along the epipolar line minimizing a cost function. A local neighbourhood around pixel (u; v) is transformed into a bit-string according to its intensity differences with:

$$T(u, v) := \bigotimes_{i=\frac{-n}{2}}^{\frac{n}{2}} \bigotimes_{j=\frac{-m}{2}}^{\frac{m}{2}} \xi(I(u, v), I(u+i, v+j)) \quad (1)$$

where I(u; v) is the intensity of (u; v), N is a bitwise catenation, (n×m) denotes the local neighbourhood. ξ is defined as:

$$\xi(x, y) := \begin{cases} 0 & \text{if } x \leq y \\ 1 & \text{if } x \geq y \end{cases} \quad (2)$$

As the cameras are mounted in a horizontal line the disclosed method minimizes for the disparity value d with the following Cost function C(u, v, d):

$$C(u,v,d) := Ham(T_a(u,v), T_b(u+d,v)) \quad (3)$$

where Ham is the Hamming distance between bit strings $T_a$ and $T_b$ of the images from camera a and b. Using disparity d, for each pixel u=(u; v) a metric point measurement p(u;v)=(x; y; z) in $R^3$ is received.

Patient Pose Estimation: The incoming range image RI is filtered using a bilateral filter on the current depth-frame to remove noise while still preserving edges. The cloud is down sampled further by discretizing the space into regular voxels of 0.3 mm³ and taking only the average of each occupied voxel. As soon as the buffer that holds the current patient model has been filled, the tracking thread starts registering the model against the prepared range image RI. Therefore, the disclosed method employs a variant of the ICP algorithm initialized with the most recent pose by incorporating the plane-to-plane metric described by Segal et al. Using the plane-to-plane metric, sliding effects can be successfully excluded which are introduced by the thorax being a larger low-frequency region in the point cloud.

Reconstruction of the Patient: As the disclosed method does not rely on pre-operative CT surface, a "close enough" initial guess of the surface in the initialization phase has to be acquired. The disclosed method takes advantage of the fact that following the clinical procedure, (i) the patient has been positioned roughly at the isocentre and in the field of view of the camera rig, and (ii) the patient is not moved in the initialization phase. Thus the disclosed method can serve to define a filter which rejects (i.e. discards) all points not being in a box sized region of 50 cm³ around the isocentre at couch level. Subsequently, the disclosed method acquires five frames and feed them directly into the patient model reconstruction thread. For all frames captured in the initialization phase the registered pose is assumed to be the origin pose. The registration result is later qualified by their residual registration error and integrate the cloud if the error is reasonably low. The incoming frame is then segmented by a simple outlier rejector that throws away (i.e. discards) points that have less than 20 neighbours in a radius of 2 cm. The disclosed method relies on the assumption that the patient is one single big cluster and other small clusters are noise and do not belong to the patient. The remaining points are assumed to belong to the patient only and will now be integrated into a single global cluster cloud representation which can be queried for either a complete version or a geometrically stable sample of the cloud (see Gelfand et al.). Having performed the initial segmentation and integrating only points that are very near to the patient model, the segmentation step can be skipped from now on. The cluster cloud is a set C of clusters $Cl_i$ with i:=1, 2, . . . , n. Each cluster has a cluster representant $c_i \in R^3$. Furthermore, there exists a variance $\sigma_i$, and a generation $g_i$ for each cluster. Querying the model will either yield the complete or a downsampled set of cluster representants from the cluster cloud. For each incoming registered frame, a nearest-neighbour search is performed on the complete version of the patient model between points $p \in R^3$ from the incoming frame and cluster representants c. Correspondences are thresholded to a maximum distance value. This shall enforce that only points correspond to each other that represent a measure of the same point in space. Each cluster $Cl_i$ which has a representant $c_i$ that has corresponding nearest point $p_j$ will be updated calculating the cumulative moving average $$c_{ig_{i+1}} = \frac{p_j + gc_i}{g_{i+1}} \quad (4)$$

where $C_{ig_{i+1}}$ denotes the updated cluster representant and $g_i$ yields how many times the cluster has been updated. The variance of the cluster can then be updated using the sum of squared differences from the current representant $c_i$ denoted as $M_2$ as shown by Welford. This can easily be incrementally updated and $$\sigma_{ig_{i+1}} = M_{2g_{i+1}}/g_{i+1} - 1 \quad (5)$$

yields the variance of the cluster in a numerically stable way. Similar to Newcombe et al., a data structure is used to fuse repeating measurements of the same scenery to improve the performance of the system. Using the cluster cloud, space is not discretized artificially. The representation can be immediately used for tracking and thus can save the step of generating a reference cloud by ray tracing a truncated signed distance function representation. On the other hand, confidence values are acquired on the measurements and thus noise can be further removed from the reference cloud. If now a reference is queried that is supposed to be used by the tracking thread, the resulting set of cluster representants can be thresholded by variance and generation. In this regard, the disclosed method relies on the assumption that representants that have been measured by several frames with low variance have a higher confidence. The downsampled version of the cluster cloud is finally sent to a buffer where it can be consumed by the tracking thread.

Figure 4:
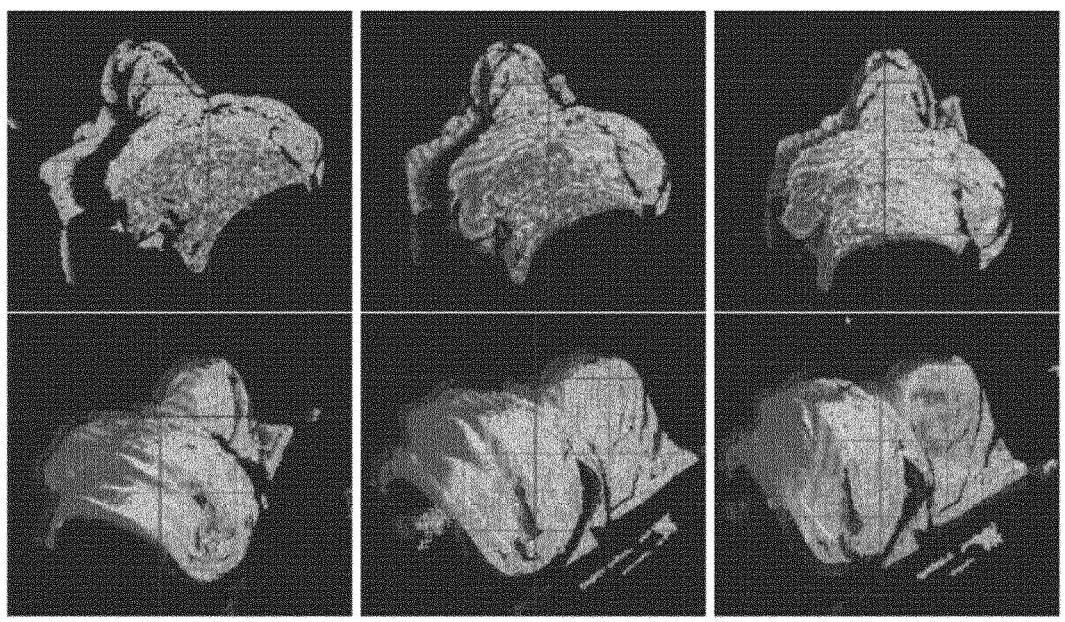
FIG. 4 shows surface evolution on a 100° patient support unit angle trajectory.

Results and Discussion: In FIG. 4, the white points are the points currently detected by the sensor. The red points are the reconstructed reference model. One can see the points are distributed all over the surface although much of the surface in the final pose was initially not visible. The algorithm in accordance with the disclosed method was evaluated using the Brainlab ExacTrac® 6.0 system. An anthropomorphic phantom was used which contains internally anthropomorphic bone structure. A CT scan was recorded and a test plan was created using Brainlab iPlan® RT 4.5. The surface was filmed using our camera setup, while the internal structure was imaged and registered against the CT scan using the stereoscopic x-ray which became our ground truth. The phantom was positioned using ExacTrac® as accurately as possible in the machine isocentre. The target registration error is evaluated separately for the translational part $TRE_{trans}$ and the rotational part $TRE_{rot}$.

$$TRE_{trans} = |||t_{alg}|| - ||t_{ref}|||$$ (6)

$t_{alg}$ is the translation computed by our algorithm and $t_{ref}$ is the translation vector computed by the stereoscopic x-ray system. Patient misalignment compensation in clinical radiation therapy should occur for shifts up to 20 mm. This happens when the patient has already been correctly positioned. The patient moves subtly if initial inner tension relieves and the patient calms down. To simulate this, the algorithm in accordance with the disclosed method was initialized to acquire the basis reference surface from which the evolution can start. In the next step, the phantom was displaced by 10 mm, 20 mm and 25 mm along each translational axis simultaneously. The length of the offset was now verified using the ExacTrac® system and he result was compared to the results of our algorithm. Results can be seen in Table 1:

TABLE 1

Target registration error for patient misalignment

| Shift (mm) | Lateral (mm) | Longnitudinal (mm) | Vertical (mm) |
|---|---|---|---|
| 10 | 0.077 ± 0.09 | 0.322 ± 0.08 | 0.527 ± 0.04 |
| 20 | 0.047 ± 0.16 | 0.389 ± 0.09 | 0.630 ± 0.05 |
| 25 | 0.160 ± 0.12 | 0.220 ± 0.17 | 0.748 ± 0.08 |

Mean target registration error for the compensation of coplanar patient misalignment was 0.44 ±0.1 mm. To evaluate for the rotational component, the couch was rotated around the x, y, z axis for 2.5°, respectively. The mean errors were for x 0.049±0.06°, for y 0.024±0.03° and for z 0.032±0.039°, respectively.

Non-coplanar field misalignment arises if CBCT is used which can only perform coplanar position correction. The patient is positioned with couch angle zero and then the couch is turned to the desired angle. A technique must be in place now to ensure the patient does not move. Furthermore if the couch is not rotating perfectly at the isocentre then non-coplanar errors occur. As stated above, the inventors believe this to be the first experimental results disseminated to the public for non-coplanar drift. To evaluate the performance of the system with respect to non-coplanar positioning, the anthropomorphic phantom was manually displaced from 0° to roughly 30° around the vertical axis of the couch while simultaneously tracking the patient. A test similar to the above-described patient misalignment test was conducted by now moving the phantom for 20 mm along the vertical axis. The algorithm in accordance with the first aspect of the disclosed method must be robust to this accumulated drift. For an absolute shift of 30° vertical and 20 mm vertical displacement, the algorithm performed here with an error of 4.88±0.721 mm.

Tracking stability with very large angles is show in FIG. 4. The algorithm tracked the phantom on roughly 100° couch rotation without falling into a local minimum. 80% of the finally reconstructed points were initially not visible. The algorithm tracked from 20,000 to 100,000 points with a frequency of roughly 2 Hz for one scanning iteration.

These results show that the method in accordance with the first aspect of the disclosed method is simple, robust and cost effective in coping with the challenges.

Figure 5:
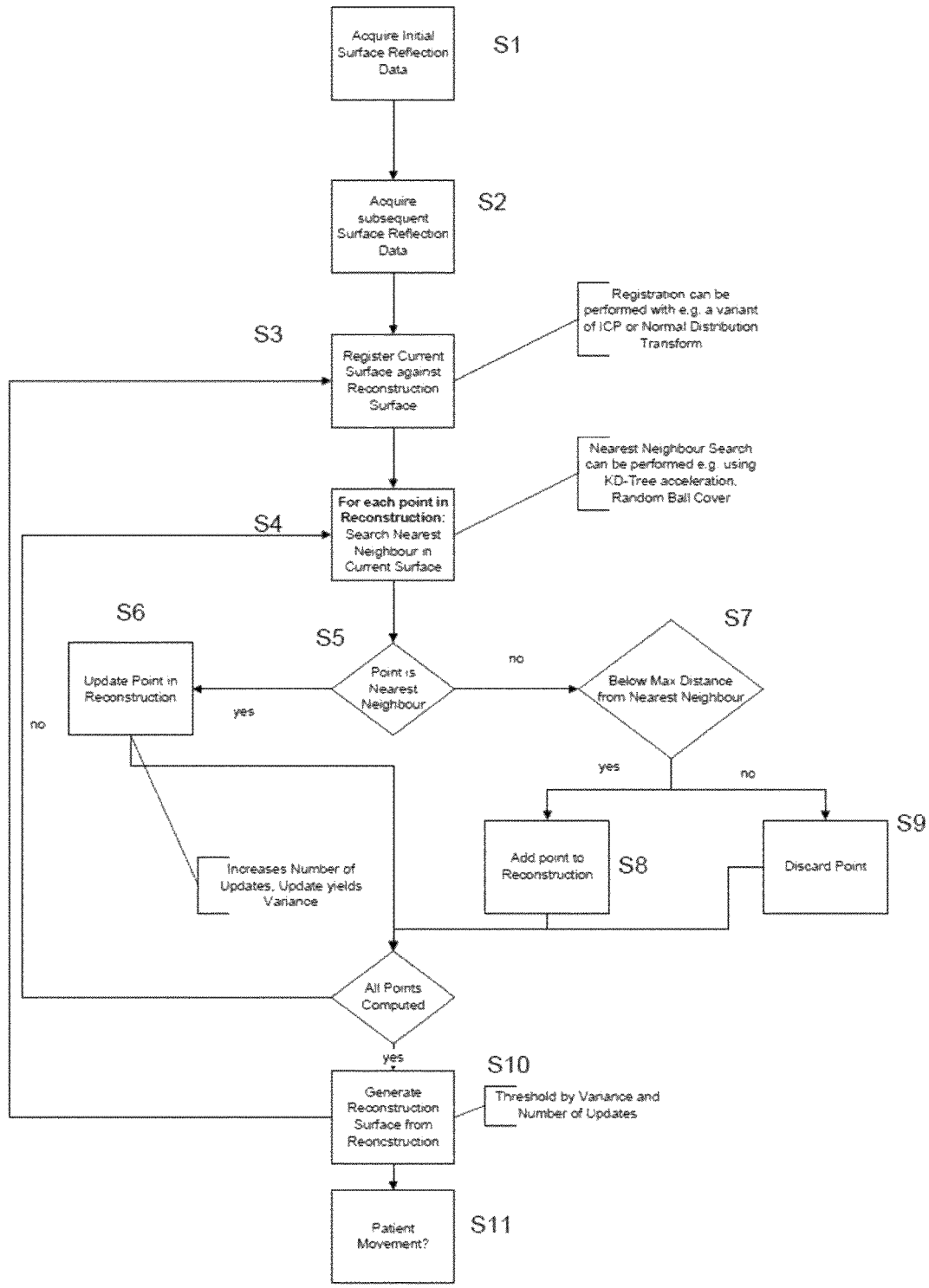
FIG. 5 is a flow diagram showing the order of steps of the method in accordance with the first aspect of the disclosed method.

FIG. 5 specifies the order of method steps in accordance with the method according to the first aspect of the disclosed method. The method starts with step S1 in which the initial surface reflection data is acquired, and continues with step S2 in which the subsequent surface reflection data is acquired. In step S3, the second reflection pattern representing a current surface (also termed subsequent part of the body surface) is then registered against (for example, transformed into the same coordinate system as and/or joined to) the initial first reflection pattern. This registration can be performed with for example an iterative closest point (ICP) algorithm, a variance distribution transform or normal distribution transform. The method then continues with step S4 which defines the entry into a loop for the nearest neighbour search which can be performed for example using KD-tree acceleration or a random ball cover algorithm. This encompasses searching, in the first reflection pattern, for a nearest neighbour for each point of the first reflection pattern included in the reconstruction. In step S5, a decision is made whether a specific point of the first reflection pattern actually is the nearest neighbour, and if this is the case, step S6 is executed which includes updating the position of the current reflection point of the first reflection pattern in the reconstruction for example by the above-described (weighted) average position. The number of updates of the reconstruction is thereby increased, and each update yields a specific variance for the positions of the current reflection points of the second reflection pattern. If step S5 results in a negative answer ("no"), step S7 is entered which is directed to determining whether the current reflection point of the second reflection pattern is within a predetermined distance from a reflection point of the first reflection pattern. If this answered in the positive, step S8 is entered and the current reflection point of the second reflection pattern is added to the reconstruction. If step S7 is answered in the negative, the current reflection point of the second reflection pattern is discarded in step S9. It is then analysed whether all points of the second reflection pattern have been processed (computed). If this results in a negative answer, step S4 is re-entered. If this analysis results in a positive answer ("yes"), a reconstruction surface is generated in step S10, which may be thresholded by the variance and number of updates. In step S11, it is then finally determined based on the just generated reconstruction surface whether the body surface has undergone a movement by determining the body surface movement data based on the estimated six-dimensional pose received from step S3 and the distance to the pose estimated in the last iteration it can be deduced if the patient has moved.

Figure 6:
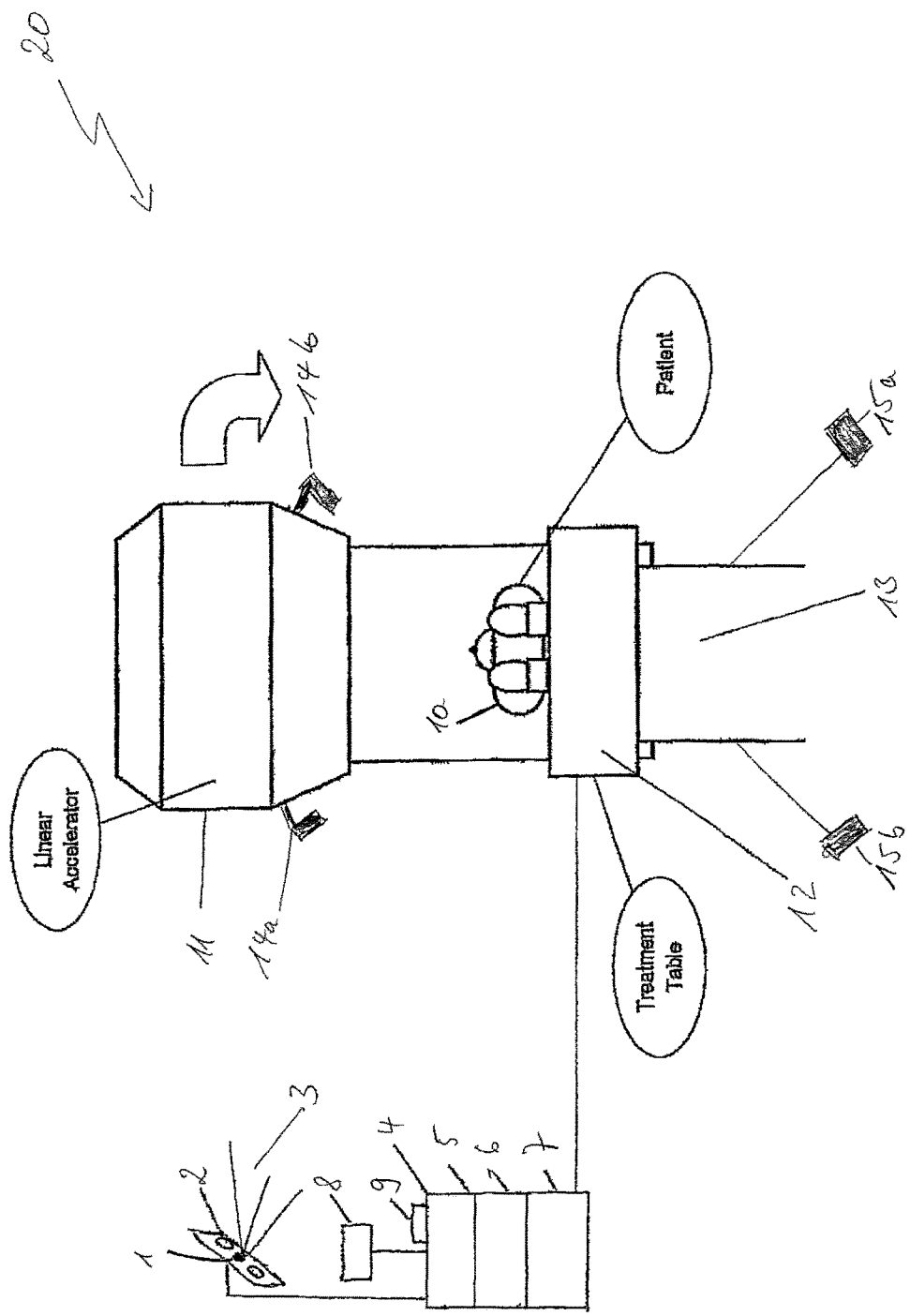
FIG. 6 shows the general setup of a radiotherapy system or radiosurgery system in accordance with the fourth aspect of the disclosed method.

FIG. 6 shows the general setup of a radiotherapy system 20 or radiosurgery system 20. The system comprises a laser light source 1 serving as a light emitting unit and a stereoscopic camera 2 serving as a reflection detection unit. The laser source 1 emits laser beams 3 onto the patient's body 10 which is placed on a treatment table 12 serving as a patient support unit. The laser unit 1 and stereoscopic camera 2 are operatively coupled to a computer 4 comprising a CPU 5, volatile memory (RAM) 6 and for example a non-volatile memory (hard disc) 7. The computer 4 is operatively coupled to an input device such as a keyboard 9 and a display device such as a monitor 8. Furthermore, the computer 4 is operatively coupled to a linear accelerator 11 serving as a treatment beam source, an x-ray tubes 14a, 14b and an x-ray detectors 15a, 15b which together serve as an imaging unit of the radiotherapy system or radiosurgery system 20 and to a movement unit 13 (comprising for example an electric motor) for moving the treatment table 12. The x-ray tubes 14a, 14b may be disposed in a movable manner on the housing of the linear accelerator 11, and the x-ray detectors 15a, 15b are for example semi-conductor based panels disposed in the floor adjacent to the treatment table 12 and/or its associated moving unit 13. The computer 4 is configured to issue control signals to moving unit (comprising for example an electric motor) for moving the treatment beam source11. The linear accelerator 11 may be rotated around the longitudinal axis of the patient's body as indicated by the curved arrow in FIG. 6. The computer 4 is configured to execute a program which may be stored on the hard disc 7 so that the method in accordance with the first or second aspect of the disclosed method is performed.

The invention claimed is:

1. A medical system, comprising:
a treatment beam source;
a patient support unit;
a light emitting unit to emit light for generating optical signals to be reflected;
a reflection detection unit for detecting the reflected optical signals;
at least one computer, the computer being operatively connected to the reflection detection unit, the light emitting unit, the treatment beam source and the patient support unit, the at least one computer having a memory and at least one processor configured to execute a program which, when executed by the processor, determines a movement of a patient's body by tracking the position of a body surface of the body, and:
acquires, at the at least one processor, initial surface reflection data describing a first reflection pattern of reflection points of optical signals emitting by the light emitting unit and reflected from an initial part of the body surface and the positions of the reflection points of the initial part at which the optical signals are reflected;
acquires, at the at least one processor, subsequent surface reflection data describing a second reflection pattern of reflection points of optical signals emitting by the light emitting unit and reflected from a subsequent part of the body surface and further describing the positions of the reflection points of the subsequent part at which the optical signals are reflected, wherein the subsequent surface reflection data is generated after the generation of the initial surface reflection data;
determines, by the at least one processor, body surface reconstruction data describing a positional reconstruction of the body surface by determining, by the at least one processor and based on the initial surface reflection data and the subsequent surface reflection data, reflection pattern registration data describing a positional registration of the second reflection pattern with the first reflection pattern;
wherein the reflection pattern registration data is determined by the at least one processor based on searching the second reflection pattern for at least one nearest neighbouring reflection point in the second reflection pattern for the reflection points in the first reflection pattern by determining, by the at least one processor and for each reflection point in the second reflection pattern, whether it is the nearest neighbour to a currently considered reflection point in the first reflection pattern, which is a current reflection point of the second reflection pattern, and,
either, if it is determined, by the at least one processor, that the current reflection point of the second reflection pattern is the nearest neighbour to a reflection point in the first reflection pattern, updates, by the at least one processor, the current reflection point of the first reflection pattern by the current reflection point of the second reflection pattern;
or, if it is determined, by the at least one processor, that the current reflection point of the second reflection pattern is not a nearest neighbour to a reflection point in the first reflection pattern, determines, by the at least one processor, whether the current reflection point of the second reflection pattern is within a predetermined distance from a reflection point of the first reflection pattern, and
either, if it is determined, by the at least one processor, that the current reflection point of the second reflection pattern is within a predetermined distance from a reflection point of the first reflection pattern, adds the current reflection point of the second reflection pattern to the reconstruction,
or, if it is determined, by the at least one processor, that the current reflection point of the second reflection pattern is not within a predetermined distance from a reflection point of the first reflection pattern, discards by the at least one processor, the current reflection point of the second reflection pattern, stores, by the at least one processor, the current reflection point of the second reflection pattern and uses the current reflection point of the second reflection pattern as initial surface reflection data in a later iteration of the method;
determines, by the at least one processor and based on the initial surface reflection data and the reflection pattern registration data, body surface movement data describing whether the body surface has undergone a movement.

2. A method for determining a movement of a patient's body by tracking the position of a body surface of the body, the method comprising:
executing, by at least one or more processors of at least one computer, the steps of:
acquiring, by the at least one or more processors, initial surface reflection data describing a first reflection pattern of reflection points of optical signals reflected from an initial part of the body surface and the positions of the reflection points of the initial part at which the optical signals are reflected;
acquiring, by the at least one or more processors, subsequent surface reflection data describing a second reflection pattern of reflection points of optical signals reflected from a subsequent part of the body surface and further describing the positions of the reflection points of the subsequent part at which the optical signals are reflected, wherein the subsequent surface reflection data is generated after the generation of the initial surface reflection data;

determining, by the at least one or more processors, body surface reconstruction data describing a positional reconstruction of the body surface by determining, by the at least one or more processors and based on the initial surface reflection data and the subsequent surface reflection data, reflection pattern registration data describing a positional registration of the second reflection pattern with the first reflection pattern, wherein the reflection pattern registration data is determined, by the at least one or more processors and based on searching the second reflection pattern for at least one nearest neighbouring reflection point in the second reflection pattern for the reflection points in the first reflection pattern by determining, by the at least one or more processors and for each reflection point in the second reflection pattern, whether it is the nearest neighbour to a currently considered reflection point in the first reflection pattern, which is a current reflection point of the second reflection pattern, and, either, if it is determined, by the at least one or more processors, that the current reflection point of the second reflection pattern is the nearest neighbour to a reflection point in the first reflection pattern, updating, by the at least one or more processors, the current reflection point of the first reflection pattern by the current reflection point of the second reflection pattern;

or, if it is determined, by the at least one or more processors, that the current reflection point of the second reflection pattern is not a nearest neighbour to a reflection point in the first reflection pattern, determining, by the at least one or more processors, whether the current reflection point of the second reflection pattern is within a predetermined distance from a reflection point of the first reflection pattern, and either, if it is determined, by the at least one or more processors, that the current reflection point of the second reflection pattern is within a predetermined distance from a reflection point of the first reflection pattern, adding the current reflection point of the second reflection pattern to the reconstruction, or, if it is determined, by the at least one or more processors, that the current reflection point of the second reflection pattern is not within a predetermined distance from a reflection point of the first reflection pattern, discarding, by the at least one or more processors, the current reflection point of the second reflection pattern, storing, by the at least one or more processors, the current reflection point of the second reflection pattern and using the current reflection point of the second reflection pattern as initial surface reflection data in a later iteration of the method;

determining, by the at least one or more processors and based on the initial surface reflection data and the reflection pattern registration data, body surface movement data describing whether the body surface has undergone a movement.

3. The method according to claim 2, wherein determining whether the current reflection point of the second reflection pattern is within a predetermined distance from a reflection point of the first reflection pattern comprises determining, by the at least one or more processors, a spatial neighbourhood around a centre point between the current reflection point of the second reflection pattern and the current reflection point of the first reflection pattern, and determining a characteristic size of the neighbourhood.

4. The method according to claim 2, wherein the positional information processed by the method is defined in three dimensions.

5. The method according to claim 4, wherein the first reflection pattern and the second reflection pattern are represented by three-dimensional point clouds.

6. The method according to claim 2, wherein updating the current reflection point of the first reflection pattern includes assigning, by the at least one or more processors, a weight to the current reflection point of the first reflection pattern, and wherein the position of any current reflection point of the second reflection pattern to be stored is assigned, by the at least one or more processors, a lower weight than the reflection points already contained in the first reflection pattern.

7. The method according to claim 2, wherein a current reflection point of the second reflection pattern having a statistically larger distance from the current reflection point of the first reflection pattern is assigned, by the at least one or more processors, a lower weight than a current reflection point of the second reflection pattern having a statistically smaller distance from the current reflection point of the first reflection pattern.

8. The method according to claim 2, wherein a current reflection point of the second reflection pattern having a statistically larger distance from the current reflection point of the first reflection pattern is not included in the reconstruction and is not stored for future use as initial surface reflection data.

9. The method according to claim 2, wherein the optical signals comprise, light signals in the infrared wavelength spectrum emitted from a light emitting unit.

10. The method according to claim 2, wherein the initial surface reflection data and the subsequent surface reflection data are acquired, by the at least one or more processors, by detecting the reflected optical signals with a reflection detection unit which is sensitive in the infrared wavelength spectrum.

11. The method according to claim 10, wherein the reflection detection unit is a stereoscopic camera, and wherein the positions of the reflection points of the first reflection pattern and of the second reflection pattern are acquired, at the at least one or more processors, based on applying, by the at least one or more processors, a triangulation algorithm to the signals detected by the stereoscopic camera.

12. The method of claim 2, further including:
at least one of the following steps:
determining, by the at least one or more processors and based on the body surface movement data, treatment beam data;
describing whether to activate or deactivate a treatment beam; or
determining, by the at least one or more processors and based on the body surface movement data, patient support unit control data for controlling a patient support unit of a radiotherapy system or a radiosurgery system, to move such that the movement of the body surface is compensated for in view of positional information contained in a predetermined treatment plan describing a treatment plan for at least one of radiotherapy or radiosurgery.

13. The method of claim 2, further including:
    determining, by the at least one or more processors and based on the body surface movement data, verification imaging;
    control data for activating an imaging unit of a radiotherapy system or a radiosurgery system to generate medical image data for verification of the position of a treatment target.

14. A non-transitory computer storage medium storing code which, when executed by at least one or more processors of at least one computer, causes the computer to execute instructions for determining a movement of a patient's body by tracking the position of a body surface of the body, the instructions further causing the at least one or more processors to:
    acquire initial surface reflection data describing a first reflection pattern of reflection points of optical signals reflected from an initial part of the body surface and the positions of the reflection points of the initial part at which the optical signals are reflected;
    acquire subsequent surface reflection data describing a second reflection pattern of reflection points of optical signals reflected from a subsequent part of the body surface and further describing the positions of the reflection points of the subsequent part at which the optical signals are reflected, wherein the subsequent surface reflection data is generated after the generation of the initial surface reflection data;
    determine body surface reconstruction data describing a positional reconstruction of the body surface by determining, based on the initial surface reflection data and the subsequent surface reflection data, reflection pattern registration data describing a positional registration of the second reflection pattern with the first reflection pattern, wherein
    the reflection pattern registration data is determined based on searching the second reflection pattern for at least one nearest neighbouring reflection point in the second reflection pattern for the reflection points in the first reflection pattern by determining for each reflection point in the second reflection pattern, whether it is the nearest neighbour to a currently considered reflection point in the first reflection pattern, which is a current reflection point of the second reflection pattern, and,
    either, if it is determined that the current reflection point of the second reflection pattern is the nearest neighbour to a reflection point in the first reflection pattern, update the current reflection point of the first reflection pattern by the current reflection point of the second reflection pattern;
    or, if it is determined that the current reflection point of the second reflection pattern is not a nearest neighbour to a reflection point in the first reflection pattern, determine whether the current reflection point of the second reflection pattern is within a predetermined distance from a reflection point of the first reflection pattern, and
    either, if it is determined that the current reflection point of the second reflection pattern is within a predetermined distance from a reflection point of the first reflection pattern, add the current reflection point of the second reflection pattern to the reconstruction,
    or, if it is determined that the current reflection point of the second reflection pattern is not within a predetermined distance from a reflection point of the first reflection pattern, discard the current reflection point of the second reflection pattern, store the current reflection point of the second reflection pattern and using the current reflection point of the second reflection pattern as a new initial surface reflection data in a later iteration of the method;
    determine based on the initial surface reflection data and the reflection pattern registration data, body surface movement data describing whether the body surface has undergone a movement.

* * * * *